United States Patent [19]

Grélat

[11] 3,978,095
[45] Aug. 31, 1976

[54] PROCESS FOR THE MANUFACTURE OF 1,4-DIAMINO-5-NITROANTHRAQUINONE

[75] Inventor: Maurice Grélat, Bettingen, Switzerland

[73] Assignee: Ciba-Geigy AG, Basel, Switzerland

[22] Filed: Nov. 5, 1975

[21] Appl. No.: 629,158

Related U.S. Application Data

[63] Continuation of Ser. No. 491,439, July 24, 1974, abandoned.

[30] Foreign Application Priority Data

July 31, 1973  Switzerland............... 11145/73

[52] U.S. Cl. ............................................. 260/378
[51] Int. Cl.² .................. C07C 97/12; C07C 97/24
[58] Field of Search .................................... 260/378

[56] References Cited

UNITED STATES PATENTS

| | | | |
|---|---|---|---|
| 2,570,866 | 10/1951 | Sargent et al. | 260/378 X |
| 3,235,549 | 2/1966 | Broussalian | 260/243 R |
| 3,646,071 | 2/1972 | Frey et al. | 260/378 |
| 3,654,319 | 4/1972 | Neff | 260/378 X |
| 3,818,052 | 6/1974 | Hohmann | 260/378 X |

FOREIGN PATENTS OR APPLICATIONS

| | | | |
|---|---|---|---|
| 268,592 | 12/1913 | Germany | 260/378 |
| 1,218,465 | 8/1963 | Germany | 260/378 |
| 1,017,869 | 1/1966 | United Kingdom | 260/378 |
| 1,033,773 | 6/1966 | United Kingdom | 260/378 |

OTHER PUBLICATIONS

BIOS Final Report, No. 1484, p. 20.

*Primary Examiner*—Paul F. Shaver
*Attorney, Agent, or Firm*—Joseph G. Kolodny; Edward McC. Roberts; Prabodh I. Almaula

[57] ABSTRACT

A process for the manufacture of 1,4-diamino-5-nitroanthraquinone from 1,4-diaminoanthraquinone by nitration with mixed nitric and sulphuric acid, before which nitration a masking of the two amino groups to form 1,9-4,10-anthraquinone disulphonimide takes place, this intermediate being in turn split by hydrolysis after the nitration, which process comprises carrying out the masking of the 1,4-diaminoanthraquinone to form the 1,9-4,10-anthraquinone-disulphonimide with liquid sulphur trioxide and carrying out the entire nitration process by using liquid solvents which are inert towards the reactants.

3 Claims, No Drawings

PROCESS FOR THE MANUFACTURE OF 1,4-DIAMINO-5-NITROANTHRAQUINONE

This is a continuation of application Ser. No. 491,439, filed on July 24, 1974, now abandoned.

The present invention provides a process for the manufacture of 1,4-diamino-5-nitroanthraquinone by nitrating 1,4-diamino-anthraquinone with nitrosulphuric acid via the intermediate 1,9-4,10-anthraquinone-disulphonimide using sulphur trioxide as masking reagent for the formation of the anthraquinone-disulphonimide, the entire nitration process being carried out in organic solvents which are intert towards the reactants.

The reaction proceeds according to the reaction scheme:

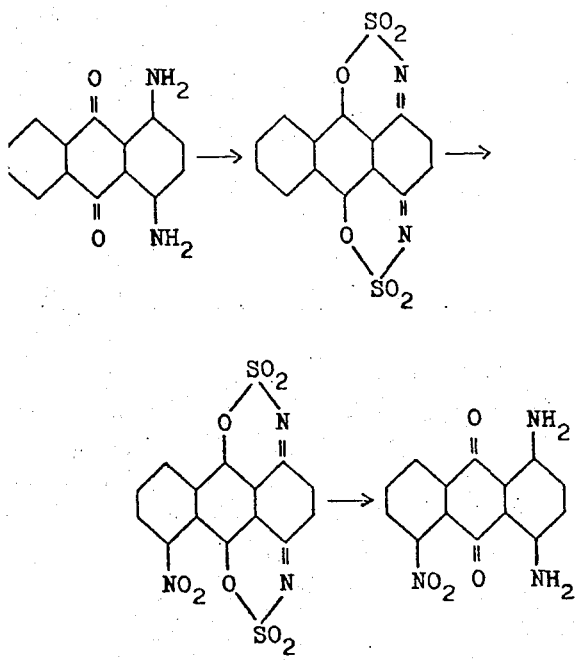

The 1,4-diamino-5-nitroanthraquinone consitutes a valuable violet dyestuff.

The process according to the steps of the above reaction scheme is known and has been described e.g. in BIOS Final Report No. 1484, p. 20.

Hitherto, oleum has been used to mask the amino groups of the 1,4-diamino-anthraquinone.

After the subsequent nitration with nitrosulphuric acid has been effected, the disulphonimide protective groups formed as intermediate are in turn split by hydrolysis using sulphuric acid.

However, the nitration of 1,4-diamino-anthraquinone to form 1,4-diamino-5-nitroanthraquinone by this known process requires large amounts of sulphuric acid or oleum which are used partly as reaction medium and partly as making reagent.

According to the particulars of the BIOS Final Report, the following amounts of sulphuric acid or oleum required for a batch of 100 kg of 1,4-diamino-anthraquinone:

a. 700.0 kg of 65% oleum as solvent medium for 1,4-diaminoanthraquinone and as masking reagent for the formation of 1,9-4,10-anthraquinone-disulphonimide.

b. 293.0 kg of 78% $H_2SO_4$ for diluting the reaction medium according to the masking reaction.

c. 86.5 kg of 100% $H_2SO_4$ in the form of nitration mixed acid containing 28% $HNO_3$.

d. 330.0 kg of 38% $H_2SO_4$ for washing the 5-nitro-1,9-4,10-anthraquinone-disulphonimide.

If the $SO_3$ content of the oleum is converted into sulphuric acid, then 1,160.0 kg of sulphuric acid are required for the above 100 kg batch in the first two steps of the process.

This sulphuric acid poses a major ecological problem since, after termination of the reaction cycle, it can probably be reused only in the rarest instances. Moreover, for commercial reasons it is preferable to use small amounts of ballast materials which are absolutely necessary in a reaction.

The present invention is based on the surprising observation that, on using liquid sulphur trioxide as masking reagent, substantially smaller amounts of waste sulphuric acid occur than in known processes. So great is the effect that it is possible to save more than 60% of the sulphuric acid normally required.

Another great advantage is the novel process is that the masked nitration product is insoluble in the reaction medium. This has advantages with regard to reaction kinetics and makes possible an exact separation of the product from the reactants without the necessity of using phase-modifying assistant, e.g. water. A product us thereby obtained direct in straightforward manner and the recovery of the reaction media is greatly eased.

The new process for the manufacture of 1,4-diamino-5-nitroanthraquinone from 1,4-diaminoanthraquinone by nitration with a mixture of nitric and sulphuric acid, before which nitration a masking of both amino groups to form the 1,9-4,10-anthraquinone-disulphonimide occurs, this intermediate being split by hydrolysis after the nitration, consists in carrying out the masking of the 1,4-diaminothraquinone to form 1,9-4,10-anthraquinone-disulphonimide with liquid sulphur trioxide and using as reaction medium for carrying out the entire nitration process liquid solvents which are inert towards the reactants.

As starting material it is possible to use both pure and commercial 1,4-diaminoanthraquinone.

Inert organic solvents which are suitable for use as reaction medium are those which are liquid at the reaction temperature applied or which become liquid through the cryoscopic temperature drop in the reaction mass and do not enter into any chemical reaction with sulphur trioxide and mixed nitric and sulphuric acid.

Preferred liquid, inert solvents are those which contain at least one $—SO_2$ group in the molecule, e.g. dimethyl sulphate, sulpholane, dimethyl sulphone, tetramethylene sulphone, hexamethylene sulphone, methyl ethyl sulphone etc.

The process according to the invention is carried out with advantage in the following manner.

The solvent is put into the reaction vessel in an amount 4 to 8 times greater by volume than the 1,4-diaminoanthraquinone to be nitrated. Then liquid sulphur trioxide is added to the solvent.

The amount of sulphur trioxide must be at least 4 moles to one mole of 1,4-diaminoanthraquinone and should not exceed 8 moles. The temperature rises adiabatically during this operation to 30°C–40°C, but this does not constitute a critical value. For example, the temperature may rise to 60°C–65°C. The 1,4- diaminoanthraquinone is subsequently added by small amounts with stirring in such manner that the temperature does not rise above 80°C. Temperatures between 50°C and 65°C are advantageous. The reaction mass is then stirred for a time - which may be from 2 to 8 hours depending on the size of the batch - at the given temperatures and subsequently cooled to about 20°C.

The subsequent nitration is effected with mixed nitric and sulphuric acid as used in the art for nitration reactions. An acid mixture containing 50% of $HNO_3$ and 50% of $H_2SO_4$ and a surplus of $HNO_3$ over the theoretically required amount of 25–30%.

It is also possible to use other acid mixtures, for example containing 20–80% of $HNO_3$. At low concentrations of $HNO_3$ the nitration proceeds too slowly and at too high concentrations too energetically. The addition of the acid mixture is effected continuously at such a speed that the reaction temperature does not exceed 25°C and it may be necessary to cool. Upon completion of the addition, stirring is continued for a time, usually from 2 to 8 hours.

The 5-nitro-anthraquinone-1,9-4,10-disulphonimide which forms during the reaction is insoluble in the reaction medium and crystallises out. It is isolated from the reaction medium by suction filtration or by other methods of separation, washed with water until neutral and dried.

The 1,4-diamino-5-nitroanthraquinone is obtained from the 5-nitroanthraquinone-1,9-4,10-disulphonimide in known manner, e.g. by saponification with 96% sulphuric acid at 120°C. The yields are between 70% and 80%.

The following tabular comparison of the reaction steps up to the 5-nitro-1,9-4,10-anthraquinone-disulphonimide illustrates the difference between the known processes and the process according to the invention in respect of process or solution sulphuric acid used, $SO_3$ values being converted to $H_2SO_4$ in each case. Each batch is one of 100 kg of diaminoanthraquinone.

parts by volume being the same as that between the gram and the cubic centimeter.

EXAMPLE 1

60 g of sulphur trioxide are added dropwise over the course of 15 minutes to 150 g of sulpholane. At the conclusion of the addition the temperature is 30°–40°C. With stirring, 23.8 g of 1,4-diaminoanthraquinone are added and the batch is kept for 4 hours at 60°–65°C. and then cooled to 20°C–25°C. At this temperature 16.5 g of 50% mixed nitric and sulphuric acid are added dropwise over the course of 2 hours and stirring is continued for 4 hours. The precipitated crystallised 5-nitro-1,9-4,10-anthraquinone-disulphonimide is filtered off, washed with water and dried. The yield is 74.5% of theory. The 1,4-diamino-5-nitroanthraquinone is obtained from the nitroanthraquinone-disulphonimide in known manner, e.g. by saponification with 96% sulphuric acid at 120°C.

EXAMPLE 2

60 g of liquid $SO_3$ are added dropwise to 100 g of dimethyl sulphone at 40°–50°C when gradually a stirrable mixture is formed. To this mixture is added with stirring 23.8 g of 1,4-diaminoanthraquinone. The reaction mixture is kept for 4 hours at 60°C–65°C and then cooled to 20°C. Then 27.5 g of mixed nitric and sulphuric acid of 30% $HNO_3$ content are added dropwise over the course of 2 hours. The nitration is brought to completion by stirring the batch for 4 hours at 20°C–25°C. The precipitated crystalline 5-nitro-1,9-4,10-anthraquinonedisulphonimide is then collected by suction filtration, washed with water until neutral and dried. The yield is 78% of theory.

The 1,4-diamino-5-nitroanthraquinone is obtained in known manner by hydrolysis of the disulphonimide groups in 96% sulphuric acid.

EXAMPLE 3

A very pure product is obtained in 80% yield by using

| | BIOS - Process | | | Process according to the invention with $SO_3$ | | |
|---|---|---|---|---|---|---|
| 1,4-diaminoanthra-quinone | | 100 kg | | | 100 kg | |
| | | $SO_3$ | $H_2SO_4$ | | $SO_3$ | $H_2SO_4$ |
| a) Oleum 65% | 500 kg | 325,0 kg | 175,0 kg | a) | | |
| | 200 kg | 130,0 kg | 70,0 kg | $SO_3$ | 252,0 kg | 252,0 kg |
| b) $H_2SO$ 78% | 293 kg | | 228,5 kg | — | | |
| c) Mixed acid 28% $HNO_3$ | 120 kg | | 86,5 kg | c) Mixed acid 50% | 69,2 kg | 34,6 kg |
| d) Washing acid 38% | 330 kg | | 125,5 kg | | | |
| - bound $SO_3$ (as disulphone) | | −67,0 kg | | - bound $SO_3$ (as disulphone) | −67,0 kg | |
| | | 388,0 kg = | 475,0 kg | | 185,0 kg = | 227,4 kg |
| Total Sulphuric acid | | | 1160,0 kg | Total Sulphuric acid | | 262,0 kg |

The mother liquor can be processed by distillation after the isolation of the 5-nitro-1,9-4,10-anthraquinonedisulphonimide. Fractions of nitric acid, solvent and a residue which contains principally sulphuric acid and impure by-products are obtained. This residue can be processed and made ecologically harmless. The obtained solvent can be returned to the process.

The following Examples illustrate the invention, the parts and percentages being by weight unless otherwise stated and the relationship between parts by weight and corresponding amounts of dimethyl sulphate as organic solvent instead of sulpholane or dimethyl sulphone and otherwise carrying out the procedure as described in Example 1 and 2.

I claim:

1. In a process for the manufacture of 1,4-diamino-5-nitro-anthraquinone from 1,4-diaminoanthraquinone by nitration with a mixture of 50% nitric acid and 50% sulphuric acid, before which nitration a masking of the two amino groups to form 1,9-4,10-anthraquinone-disulphonimide takes place, this intemediate being in turn split by hydrolysis after the nitration, the improvement comprising the steps of (1) carrying out the masking of the 1,4-diaminoanthraquinone with liquid sulphur trioxide in a medium of inert liquid solvents to form 1,9-4,10-anthraquinone-disulphonimide in the medium, said sulphur trioxide being in an amount of 4 to 8 mols to 1 of 1,4-diaminoanthraquinone and (2) carrying out the nitration of the formed 1,9-4,10-anthraquinone-disulphonimide in said medium with a mixture of 50% nitric acid and 50% sulphuric acid, said mixture of acids being in amounts below 100 kilogram per 100 kilogram of 1,4-diaminoanthraquinone.

2. A process according to claim 1, which comprises the use of those inert, liquid organic solvents which contain in the molecule at least one $-SO_2$ group.

3. A process according to claim 2, which comprises the use of dimethyl sulphate, sulpholane, dimethyl sulphone, methyl ethyl sulphone, diethyl sulphone, tetramethyl sulphone, hexamethylene sulphone as inert, liquid solvents.

* * * * *

UNITED STATES PATENT AND TRADEMARK OFFICE
CERTIFICATE OF CORRECTION

PATENT NO. : 3,978,095
DATED : August 31, 1976
INVENTOR(S) : MAURICE GRELAT

It is certified that error appears in the above-identified patent and that said Letters Patent are hereby corrected as shown below:

Column 5, claim 1, line 6, insert after "8 mols to 1" --- mol ---.

Signed and Sealed this

First Day of February 1977

[SEAL]

Attest:

RUTH C. MASON
Attesting Officer

C. MARSHALL DANN
Commissioner of Patents and Trademarks